United States Patent [19]

Schmitt

[11] Patent Number: 5,527,353
[45] Date of Patent: Jun. 18, 1996

[54] IMPLANTABLE TUBULAR PROSTHESIS

[75] Inventor: Peter J. Schmitt, Garnerville, N.Y.

[73] Assignee: Meadox Medicals, Inc., Oakland, N.J.

[21] Appl. No.: 161,648

[22] Filed: Dec. 2, 1993

[51] Int. Cl.⁶ ................................. A61F 2/06; A61F 2/04
[52] U.S. Cl. .................................................. 623/1; 623/12
[58] Field of Search ................................. 623/1, 11, 12; 600/36; 606/151–158, 194–195

[56] References Cited

U.S. PATENT DOCUMENTS

| Re. 31,618 | 7/1984 | Mano et al. . | |
|---|---|---|---|
| 3,688,317 | 9/1972 | Kurtz | 623/1 |
| 3,914,802 | 10/1975 | Reick | 3/1.4 |
| 4,130,904 | 12/1978 | Whalen . | |
| 4,286,341 | 9/1981 | Greer et al. | 623/1 |
| 4,306,318 | 12/1981 | Mano et al. . | |
| 4,416,028 | 11/1983 | Eriksson et al. . | |
| 4,441,215 | 4/1984 | Kaster . | |
| 4,604,762 | 8/1986 | Robinson . | |
| 4,623,842 | 12/1986 | Karwoski et al. | 427/2 |
| 4,738,740 | 4/1988 | Pinchuk et al. | 156/167 |
| 4,816,339 | 3/1989 | Tu et al. . | |
| 4,822,361 | 4/1989 | Okita et al. . | |
| 4,850,999 | 7/1989 | Planck | 623/1 |
| 4,857,069 | 8/1989 | Kira | 623/1 |
| 4,878,908 | 11/1989 | Martin et al. | 623/1 |
| 4,892,539 | 1/1990 | Koch | 623/1 |
| 4,941,870 | 7/1990 | Okada et al. | 623/1 |
| 4,986,831 | 1/1991 | King et al. | 623/1 |
| 4,997,440 | 3/1991 | Dumican | 623/1 |
| 5,061,276 | 10/1991 | Tu et al. | 623/1 |
| 5,078,726 | 1/1992 | Kreamer | 623/1 |
| 5,084,065 | 1/1992 | Weldon et al. | 623/1 |
| 5,116,360 | 5/1992 | Pinchuk et al. | 623/1 |
| 5,118,524 | 6/1992 | Thompson et al. . | |
| 5,163,951 | 11/1992 | Pinchuk et al. . | |
| 5,178,630 | 1/1993 | Schmitt | 623/1 |
| 5,192,311 | 3/1993 | King et al. . | |

FOREIGN PATENT DOCUMENTS

| 0160483 | 11/1985 | European Pat. Off. . | |
|---|---|---|---|
| 0382158A1 | 8/1990 | European Pat. Off. . | |
| 0492481A1 | 7/1992 | European Pat. Off. . | |
| 0509814A3 | 10/1992 | European Pat. Off. . | |
| 2635966 | 3/1990 | France . | |
| 2322611 | 2/1974 | Germany | 623/1 |
| 2092894 | 8/1982 | United Kingdom . | |
| WO92/10218 | 6/1992 | WIPO . | |

Primary Examiner—Debra S. Brittingham
Attorney, Agent, or Firm—Hoffmann & Baron

[57] ABSTRACT

The present invention provides a soft-tissue prosthesis which is formed from a tubular textile substrate and a liner. The liner is affixed to the intraluminal surface of the tubular textile portion of the soft-tissue prosthesis to form a fluid-tight barrier on the intraluminal surface of the prosthesis. The liner is preferably formed from a polymer. Thus, the soft-tissue prosthesis formed in accordance with the present invention provides the advantages of both a textile prosthesis and a polymer prosthesis.

14 Claims, 1 Drawing Sheet

IMPLANTABLE TUBULAR PROSTHESIS

BACKGROUND OF THE INVENTION

1. Field of the Invention

The present invention relates to an implantable tubular prosthesis having a textile substrate with a fluid-tight microporous lining.

2. Description of the Prior Art

Tubular prostheses are commonly used as vascular grafts to replace damaged or diseased veins and arteries. To maximize the effectiveness of any prosthesis, it is desirable that the prosthesis have characteristics which closely resemble that of the natural body lumen which it is replacing.

Presently, conventional tubular prostheses and, more specifically, vascular grafts are formed by either weaving, knitting or braiding synthetic fibers into a tubular structure or using a polymer such as polytetrafluoroethylene to create a tubular structure for use as a prosthesis. Tubular textile structures have the advantage of being naturally porous, which allows desired tissue ingrowth and assimilation into the body. Porosity must be balanced to allow for ingrowth of surrounding tissue, yet minimize leakage during the initial implantation. Attempts to control porosity and provide a sufficient fluid barrier have focused on tighter stitch construction such as knitted or woven double-velours and biodegradable natural coatings such as collagen or gelatin. While these grafts sought to overcome the difficulties in achieving the porosity/fluid-tight balance, they failed to adequately address the natural tendency of tubular structures to kink or collapse when the graft is twisted or bent during or subsequent to implantation. Thus, the prior art solutions to the porosity/fluid-tight balance left unanswered the problems of kinking and overall handling.

One conventional solution to the kinking and collapsing problems has focused on the reinforcement of the prosthesis walls using reinforcing fibers, rings, or bands circumferentially placed on the tubular structure. Additional reinforcement of this kind, however, has the disadvantage of reducing the radial and/or longitudinal compliance of the graft due to the increased stiffness of the reinforcing member. A reduction in compliance reduces the area through which blood can flow, thereby compromising the ability of the prosthesis to adjust to body conditions and perform naturally. Additionally, reinforcing members are generally made from solid structural materials which cannot be penetrated by cellular ingrowth from surrounding tissue and may even cause the erosion of the surrounding tissue during contraction.

Another method of increasing the kink and crush resistance of textile grafts is to crimp the graft, i.e., longitudinally compress the tubular structure. Crimping is generally described in U.S. Pat. No. 3,142,067. While crimping serves to add a dimension of kink and crush resistance to the graft, the intraluminal surface formed by crimping includes peaks and valleys which create hemodynamic turbulence within the graft as blood passes therethrough. This turbulence affects the rate of flow and the peaks and valleys formed on the intraluminal surface contribute to excessive thrombus formation and deposition of plaque.

Another disadvantage of presently available tubular textile prostheses, in particular woven and braided grafts, is that sutures tend to pull out or tear the fabric thereby making it difficult to attach the prosthesis to the existing body lumen and to prevent leakage at this junction. Furthermore, textile tubular prostheses formed from a synthetic yarn tend to have ends of the tube which easily ravel. Once the ends ravel or fray, suturing to the existing body lumen becomes extremely difficult.

Microporous tubing formed by stretching polytetrafluoroethylene (PTFE) has also been used as implantable prostheses and especially as vascular grafts. PTFE porous tubes are considered by some to be superior in certain respects to conventional prostheses made of knitted or woven fabrics. The stretched or expanded PTFE tube has a microfibrous structure defined by the presence of nodes inter-connected by fibrils. While PTFE grafts have the advantage of being generally fluid-tight without the use of pre-clotting or specialized coatings, these grafts have limitations in their tear and tensile strength and compliance properties. PTFE grafts often require wrapping with a reinforcing support film to improve undesirable dilation. Reinforcement materials tend to impede the ingrowth of tissue necessary for rapid healing. In addition, PTFE grafts tend to be noncompliant as compared to textile grafts and natural vessels, thereby lacking many of the mechanical properties advantageous to textile grafts.

From the previous discussion it is apparent that both conventional textile prostheses and PTFE prostheses have respective benefits and disadvantages, but neither offers properties which solve all of the aforementioned problems.

Accordingly, it would be advantageous to provide a new and improved implantable tubular prosthesis which combines the best attributes and properties of each of the conventional grafts. More specifically, it would be particularly desirable to form a prosthesis which has the following characteristics: an outer surface porosity which encourages tissue ingrowth into the prosthesis; ravel and fray resistance for better suture retention and tailoring; longitudinal compliance for ease of implantation, sizing and natural vessel simulation; and a fluid-tight lumen without the need for pretreating, coating or pre-clotting.

SUMMARY OF THE INVENTION

The present invention addresses aforementioned the problems associated with the prior art and provides a soft-tissue implantable prosthesis in the form of a composite structure including a textile substrate and an integrated polymeric liner. The textile substrate includes an intraluminal surface having the liner affixed thereto, thereby rendering the tubular prosthesis fluid-tight. Accordingly, the outer surface formed by the textile substrate has the advantage of sufficient pore size to enhance tissue ingrowth and promote healing as well as other advantages associated with textile prostheses, such as flexibility and kink resistance. The liner provides a smooth, fluid-tight lumen to enhance fluid flow and which is made from a polymeric material which is naturally anti-thrombogenic.

The liner formed in accordance with the present invention is preferably formed from a polymeric material. Typical polymers for use in making the liner include, but are not limited to polytetrafluoroethylene, urethanes, silicones and polyesters. Preferably, expanded polytetrafluoroethylene is used to form the liner thus creating a microporous structure. The liner wall thickness need only be thick enough to provide a fluid-tight barrier to the intraluminal surface of the textile substrate. Thus, liner wall thicknesses are preferably thin and on the order of about 10 to about 50 microns.

The textile substrate formed in accordance with the present invention may be made by weaving, knitting or braiding yarns to form a tubular structure. In the preferred embodiment, the composite prosthesis including the textile substrate and the liner is heat conditioned to fuse the liner to the textile substrate. Thus, in one embodiment the textile substrate is formed from fibers having a melting temperature and bonding compatibility substantially similar to a material forming the liner.

In an alternative embodiment, the textile substrate may include a fusible fiber having a low melting temperature, the fusible fiber flowing onto the liner when melted for securing the liner to the textile substrate. In the case where expanded PTFE is used to form the liner, it is preferable that the fusible fiber have melt flow properties which allow the melted fiber to flow into the pores of the liner to secure the liner to the textile substrate.

In yet another embodiment, the textile substrate may be formed from any known fiber and the liner may be affixed to the substrate using an adhesive, by sewing the components together or by any other mechanical coupling means.

The textile substrate formed in accordance with the present invention may be formed by warp knitting to create a velour surface. The loops forming the velour surface are preferably on a the exterior surface to create a single-velour fabric. Single-velour fabrics have many favorable properties with respect to porosity, compliance, and suture retention.

Furthermore, the textile substrate may be formed from yarns, rovings, tapes or other stranded materials. Some of the yarns may be bioabsorbable while other yarns are merely biocompatible. Bioabsorbable yarns are preferably used to create an initial porosity different from the porosity once the bioabsorbable material has been absorbed into the body. For example, once a bioabsorbable yarn is absorbed into the body, a void or pore remains in its place. Additionally, the yarns used to form the textile substrate may be flat, twisted, textured or preshrunk.

The invention is also directed to a process for preparing a soft-tissue prosthesis. The process includes the steps of winding a polymer over a smooth mandrel to form a cylindrically-shaped liner, positioning a tubular textile substrate over an outer surface of the liner, heating the liner and textile substrate to a temperature sufficient to melt a portion of one of either the textile substrate or liner and cooling the textile substrate and liner thereby fusing the liner to the textile substrate.

In one embodiment, the textile substrate may be formed from a material which has a similar melting temperature and bonding compatibility to that of the liner. In an alternative embodiment, the liner is formed from expanded PTFE and the textile substrate includes a meltable yarn such that the molten yarn flows into the pores of the liner and, when cooled, fuses the liner to the textile substrate.

The present invention is also directed to a method of repairing a diseased blood vessel of a patient. The method includes removing a diseased portion of a blood vessel from the patient leaving a first and second open end of the blood vessel, inserting a tubular prosthesis between the first and second end of the blood vessel, the tubular prosthesis being formed from a textile substrate having an intraluminal surface and a liner affixed to the intraluminal surface of the textile substrate such that the liner renders the tubular prosthesis blood-tight, and securing the tubular prosthesis to the first and second open ends of the blood vessel to form a continuous lumen through which blood may flow.

Thus, the present invention overcomes many of the shortcomings associated with prior art soft-tissue prostheses. The soft-tissue prosthesis formed in accordance with the present invention utilizes the advantages of both a textile prosthesis and a polymer prosthesis to create a composite structure having a smooth, fluid-tight intraluminal surface yet providing a porous outer structure to encourage ingrowth of connective tissue and promote healing.

A preferred form of the textile substrate having a fluid-tight liner, as well as other embodiments, features and advantages of this invention will be apparent from the following detailed description of illustrative embodiments thereof, which is to be read in connection with the accompanying drawings.

DETAILED DESCRIPTION OF THE INVENTION

The present invention addresses the problems associated with prior art textile prostheses and tubular prostheses formed from polymers and provides a tubular prosthesis in the form of a composite structure including a textile substrate and a polymer lining affixed to an internal lumen of the substrate. The prosthesis formed in accordance with the present invention overcomes many of the disadvantages of presently available conventional tubular prostheses including controlling the porosity at the intraluminal and extraluminal surfaces of the prosthesis, while also providing a prosthesis which has enhanced ravel and fray resistance and better suture retention capabilities. Furthermore, the present invention provides a tubular prosthesis which can be designed to have characteristics closely resembling the properties of a natural body lumen.

For purposes of this application, a tubular, soft-tissue prosthesis is defined as any artificial substitute for a natural body lumen such as a vein, artery, esophagus or a bile duct. Although some of the discussion in the preferred embodiment of this invention describes a vascular graft, it is envisioned that the composite structure including a textile substrate having a polymer lining formed in accordance with the present invention can be useful as a prosthesis for any soft-tissue body lumen. Naturally, the composite structure would be designed to meet the specific requirements of the body lumen it is replacing.

Figure 1:
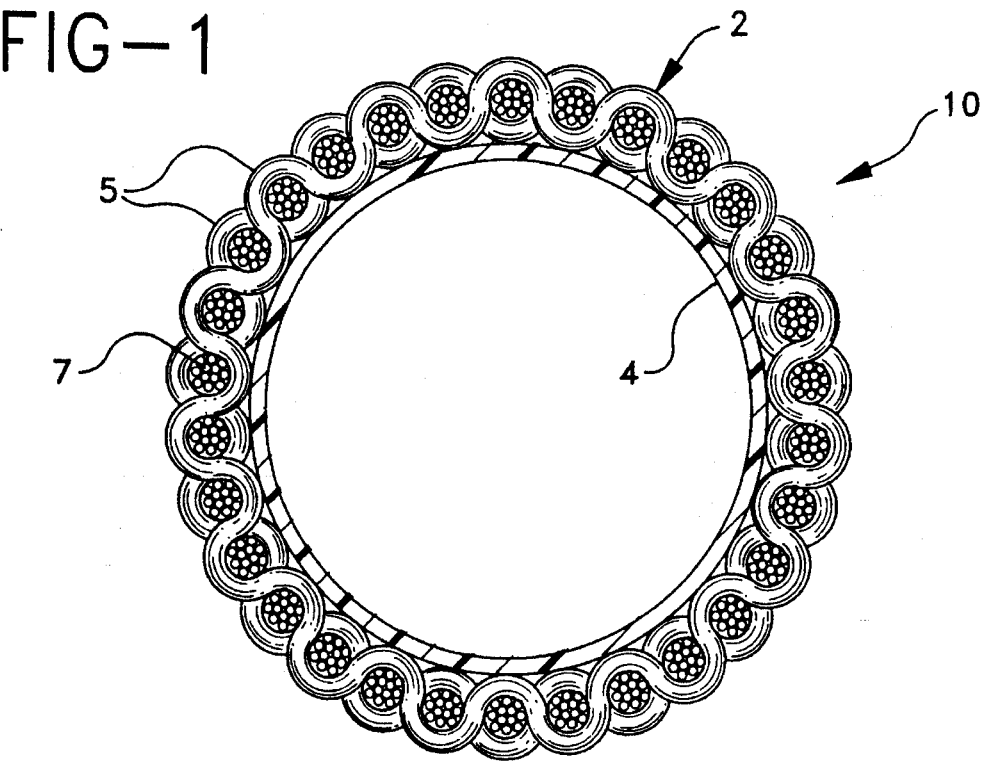
FIG. 1 is a cross-sectional view of a tubular prosthesis formed in accordance with the preferred embodiment of the present invention.
Figure 2:
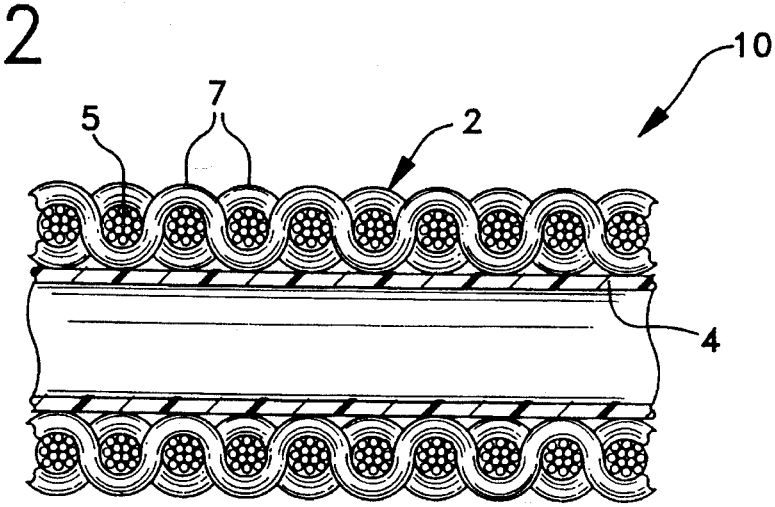
FIG. 2 is a longitudinal cross-sectional view of a tubular prosthesis formed in accordance with the preferred embodiment of the present invention.

Referring to FIG. 1, the soft-tissue prosthesis of the preferred embodiment of the present invention comprises a textile supporting sleeve 2 formed in the shape of a tube and a tubular polymer lining 4 which is affixed to an internal lumen of the textile supporting sleeve 2. The polymer lining 4 may be affixed to the textile supporting sleeve by adhesively laminating, separately sewing, meltably fusing or otherwise connecting the two components. The composite structure of the present invention 10 thus provides a soft-tissue prosthesis having the advantages of a textile prosthesis with respect to outer surface porosity, compliance and flexibility, yet the thin polymer lining 4 provides a smooth, fluid-tight internal lumen for the composite structure 10.

FIG. 1 is a cross-sectional view of a polymer lined textile soft-tissue prosthesis formed in accordance with the present invention. FIG. 1 illustrates a woven textile supporting sleeve 2 which is woven from a plurality of warp ends 5 and filling yarn 7. The textile supporting sleeve 2 may be formed by knitting, weaving or braiding a tubular structure having a desired outer diameter to correspond to the body lumen for which it is replacing. The tubular textile sleeve 2 provides the soft-tissue prosthesis with mechanical strength, suture retention, perigraft tissue attachment, radial support and kink resistance.

As illustrated in FIG. 1, the tubular textile substrate 2 is lined with a polymer to create a fluid-tight barrier through the lumen of the composite structure 10. The liner 4 formed in accordance with the preferred embodiment is preferably fluid-tight yet microporous. Furthermore, the liner 4 provides a very smooth inner surface which enhances fluid flow through small caliber soft-tissue prostheses. In the preferred embodiment, the lining 4 is formed from expanded polytetrafluoroethylene (ePTFE) although a variety of polymers may be used. Furthermore, it would not be necessary for the liner to have a large wall thickness since it is acting as a fluid barrier and not as a support structure. Accordingly, a thin liner of about 10 to about 50 microns may be used. As previously described, the polymer liner may be affixed to the textile substrate by any mechanical means such as stitching or use of an adhesive. Preferably, the liner is affixed to the textile substrate by heat conditioning the composite structure 10 to fuse the liner 4 to the intraluminal surface of the tubular textile substrate 2.

The composite soft-tissue prosthesis formed in accordance with the present invention provides an implantable body lumen having characteristics which more closely resemble that of a natural body lumen in comparison to conventional polymer prostheses and textile prostheses. For example, a vascular graft formed in accordance with the present invention includes a liner 4 which forms the intraluminal surface of the structure to be a smooth surface having a low porosity to prevent leakage of blood and the formation of excessive thrombus on the intraluminal surface. Conversely, the textile sleeve 2 can be woven, knitted or braided to have a greater porosity or even a textured surface to enhance the ingrowth of connective tissue into the vascular graft. Additionally, the vascular graft may be formed having a relatively small diameter (less than about 6 mm) yet provide enhanced fluid flow due to the smooth liner 4 and tissue ingrowth due to the porosity of the textile sleeve 2.

In a preferred embodiment, the textile substrate 2 may be formed by weaving to create a velour surface. A single-velour surface is created by a weaving technique described in commonly-owned U.S. Pat. No. 5,178,630, entitled, "Ravel-Resistant, Self-Supporting Woven Graft", the disclosure of which is incorporated herein by reference.

Figure 3:
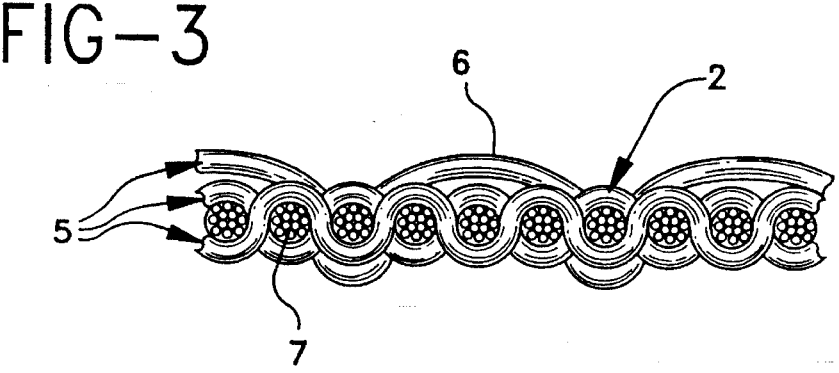
FIG. 3 is an illustration of a single-velour fabric used in accordance with an embodiment of the present invention.

Referring to FIG. 3, the textile substrate 2 may be woven having a yarn 6 which passes back and forth through a wall or trellis of the fabric forming a loop. These loops constitute the velour or pile. The loops are formed on a single surface i.e. the exterior surface, to create a single-velour fabric. The yarn 6 is pulled tight on the inner surface of the textile substrate to create a somewhat smooth surface. The liner 4 of the preferred embodiment may be adhesively laminated, separately sewn, meltably fused or otherwise connected to the intraluminal surface of the single-velour substrate of the preferred embodiment of the present invention. The woven single-velour textile substrate includes the advantages of being inherently kink resistant, strong, longitudinally flexible, non-crimped and high in suture retention. The single-velour substrate may be woven from any type or combinations of fibers, including but not limited to polyesters, polypropylenes and polytetrafluoroethylenes.

In an alternative embodiment, the tubular textile substrate 2 may also include a fiber comprising a meltable fusible material. The fusible fiber may be added to the textile substrate to aid in preventing ravelling or fraying which may occur at the ends of the textile tube. In such an embodiment, the textile tube including the fusible fiber, is heated to melt the fusible fiber onto the surrounding yarns thereby further enhancing the ravel and fray resistance of the textile structure and providing a more suitable structure for suturing to a natural body lumen.

The tubular textile substrate 2 formed in accordance with the present invention may be woven, knitted or braided from yarns, rovings, tapes or other stranded material. Some of the yarns may be bioabsorbable while other yarns are merely biocompatible. By utilizing non-woven tapes, such as spun-bonded fabric slit into, for example, 1/16' widths, a structure having excellent suture retention may be formed. In this regard, the spunbonded tape is readily pierced by a suture needle yet possesses high tear strength and positive anchoring.

As mentioned above, the textile substrate 2 of the composite soft-tissue prosthesis 10 formed in accordance with the present invention may include one or more yarns formed from bioabsorbable materials. Suitable bioabsorbable materials include but are not limited to poly (glycolic acid), poly (lactic acid), polydioxanoes, polyoxalates, poly ($\alpha$-esters), polycarbonates, polyanhydrides, polyacetals, polycaprolactones, poly (orthoesters), polyamino acids, polyurethanes, polyaminocarbonates, polyamindes, poly (alkyl cyanoacrylates), sebacic acid, polyethylene glycol, polyphosphazene, bis (p-carboxy-phenoxy) propane, bis (p-carboxyphenoxy) methane and copolymers and mixtures thereof, provided that these materials can be formed into a fiber suitable for use with the knitting, weaving or braiding apparatus being used.

A single or multiple bioabsorbable yarn may be used in the textile portion of the composite soft-tissue prosthesis. Thus, the initial porosity will increase once the bioabsorbable material has been absorbed into the body.

In the preferred embodiment of the present invention, synthetic yarns are used to form the textile portion of the composite soft-tissue prosthesis. The yarns may be flat, twisted, textured or pre-shrunk. Preferably, the yarns are made from thermoplastic materials including, but not limited to, polyesters, polypropylenes, polyethylenes, polyurethanes and polytetrafluoroethylenes and the like. The yarns may be of the multifilament, monofilament or spun type. Multifilaments are preferred to increase flexibility. Where enhanced crushed resistance is desired, the use of monofilaments has been found to be effective.

Additionally, the yarn type and yarn denier for the textile portion of the composite soft-tissue prosthesis may be chosen to meet the design requirements (porosity, flexibility and compliance) of the prosthesis, e.g. vascular graft, being formed. Yarn denier denotes the linear density of the yarn (number of grams mass divided by 9,000 meters of length). Thus a yarn having a small denier, e.g 20, would correspond with a very fine yarn, whereas a yarn having a large denier, e.g. 1000, would correspond to a heavy yarn. The yarns used to form the textile portion of the present invention may have a denier from about 20 to about 1000, and preferably from about 40 to about 300.

The type of yarn chosen and the denier of the yarn are important in order to form a soft-tissue prosthesis and, more specifically, a vascular graft having proper pore size. As previously emphasized, porosity is important when designing a vascular graft because the intraluminal surface must have pores small enough to prevent the graft from leaking blood, while the outer surface must have pores large enough to permit ingrowth of connective tissue and promote healing. The composite soft-tissue prosthesis of the present invention is particularly well suited to have proper pore sizing on both the intraluminal surface and outer surface since the composite structure utilizes the benefits of both textile and polymeric extrusion type prostheses. Thus, the polymer lining 4 provides a smooth, microporous intraluminal surface which is substantially fluid or blood-tight. Additionally, the smooth intraluminal surface reduces excessive formation of thrombus and promotes fluid flow therethrough. The outer surface is formed from a textile substrate 2 having pores large enough to permit connective tissue ingrowth into the soft-tissue prosthesis to promote healing. Since the textile substrate is lined with a thin polymer, there is no further need to treat, coat or impregnate the textile substrate to make it leak-resistant.

In an alternative embodiment of the present invention, axial yarns may be dyed and inserted into the textile portion of the soft-tissue prosthesis. The colored axial yarn positioned on the outer surface of the prosthesis aids the surgeon during implantation to indicate whether the prosthesis is accurately aligned during the procedure. Preferably, the dyed axial yarn is black in color, formed from yarns of 40–300 denier.

A composite soft-tissue prosthesis formed in accordance with the present invention may be made by first choosing a mandrel with an outside diameter corresponding to an inside diameter of a natural body lumen which is to be replaced. The mandrel preferably has a smooth outer surface. The liner may be produced from expanded PTFE film or other suitable polymer, which has been slit into a narrow tape (3–10 mm). The expanded PTFE tape is wound onto the smooth mandrel to form the liner. The textile substrate is made having an inner diameter close to the outer diameter of the expanded PTFE liner and is positioned over the liner while the liner is still on the mandrel. The entire assembly may be placed into an oven at a sufficiently high temperature to fuse the textile substrate to the polymeric liner. Generally, this heat-conditioning causes the prosthesis to shrink slightly and densify. The heat-conditioning parameters are chosen based upon the properties of the synthetic materials being used to form the textile substrate and the polymer lining. Typically, heat-conditioning is carried out at a temperature range from about 125° C. to about 225° C. using a convection oven for a time of about twenty minutes. Other means of fusing the liner to the fabric substrate may also be used, such as the use of an adhesive.

An alternative method of making the composite soft-tissue prosthesis formed in accordance with the present invention includes forming a thin wall tubular liner by extruding a polymer. A textile substrate is made having an inner diameter close to the outer diameter of the polymeric liner. The textile sleeve is passed over the liner and heat conditioned to fuse the liner within the textile substrate.

Yet another method of forming the composite soft-tissue prosthesis formed in accordance with the present invention includes dip-casting a polyurethane resin onto a mandrel to form the liner. The textile substrate is dimensioned to be passed over the dip-casted polyurethane liner. The composite structure is preferably heat conditioned to fuse the textile substrate to the polyurethane liner. The methods for making the composite soft-tissue prosthesis described herein are merely illustrative of several methods of manufacturing a prosthesis formed in accordance with the present invention. It will be obvious to those skilled in the art that alternative methods of making the composite soft-tissue prosthesis of the present invention may be used without departing from the scope or spirit of the invention.

In order for the textile substrate and polymer liner to meltably fuse together, the textile substrate may be formed from fibers which are similar in melting temperature and bonding compatibility to that of the polymer liner. For example, the textile substrate may be made from fibers such as PTFE, ethylene chlorotetrafluoroethylene, fluorinated ethylene-propylene (FEP) or polyvinyl flouride. Alternatively, the textile substrate may also incorporate a bi-component fiber having a core formed from polyethylene terephthalate polyester and a sheath formed from a resin of co-polyester, polyethylene or co-polyethylene. The sheath of the bi-component fiber melts when heated and provides enough adhesive properties to bond the textile substrate securely to the polymer liner. If an expanded PTFE liner is utilized, it has a microporous structure formed during stretching. Thus, the melted textile core of the bi-component fiber may flow into the pores of the liner mechanically bonding the textile substrate to the PTFE liner. Fusible fibers are chosen for their melt flow properties which allow for interstitial adhesion and formation of an integral composite.

The present invention is also directed to a method of repairing a diseased body lumen of a patient. The method includes the steps of removing a diseased portion of the body lumen from the patient thus leaving a first and second open end of the body lumen. A composite tubular soft-tissue prosthesis formed in accordance with the present invention is inserted between the first and second end of the body lumen. The composite tubular prosthesis is formed from a textile substrate having an intraluminal surface and a liner affixed thereto to render the tubular prosthesis fluid-tight. The inserted tubular prosthesis is secured to the first and second open ends of the body lumen to allow fluid to flow therethrough.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A soft tissue, implantable, tubular prosthesis comprising:

a first component comprising a tubular textile substrate consisting essentially of a single material and having an intraluminal surface; and a second component comprising a smooth, microporous liner positioned within and directly in contact with said intraluminal surface of said textile substrate wherein said liner renders the tubular prosthesis substantially fluid-tight and wherein the textile substrate includes fibers having a melting temperature and bonding compatibility substantially similar to a material forming said liner, wherein said liner and said textile substrate are fusibly attached upon application of heat.

2. A soft-tissue prosthesis as defined in claim 1, wherein the liner is formed from a polymer.

3. A soft-tissue prosthesis as defined in claim 2, wherein the polymer is selected from the group consisting of polytetrafluoroethylene, urethanes, silicones, polyester and mixtures thereof.

4. A soft-tissue prosthesis as defined in claim 2, wherein the polymer is expanded polytetrafluoroethylene.

5. A soft-tissue prosthesis as defined in claim 1, wherein the liner includes an inner surface and an outer surface defining a wall thickness, said wall thickness being sufficient to make the tubular prosthesis fluid-tight.

6. A soft-tissue prosthesis as defined in claim 1, wherein the textile substrate is selected from the group consisting of woven, knitted or braided yarns to form a tubular structure.

7. A soft-tissue prosthesis as defined in claim 6, wherein the textile substrate is formed from a thermoplastic polymer.

8. A soft-tissue prosthesis as defined in claim 7, wherein the thermoplastic polymer is selected from the group consisting of polyesters, polytetrafluoroethylene, polyethylenes, polyurethanes, polypropylenes and mixtures thereof.

9. A soft-tissue prosthesis as defined in claim 1, wherein the textile substrate includes at least one bioabsorbable component.

10. A soft-tissue prosthesis as defined in claim 1, wherein the textile substrate includes a colored axial yarn as a visual alignment aid during implantation.

11. A soft-tissue prosthesis as defined in claim 1, wherein the textile substrate includes a fusible fiber having a low melting temperature, lower than the textile substrate such that when heated, the fiber fuses to said liner.

12. A soft-tissue prosthesis as defined in claim 11, wherein the liner contains micropores and wherein the fusible fiber has melt flow properties which allow the melted fiber to flow into the micropores of the liner, thereby securing said liner to said textile substrate.

13. A soft-tissue prosthesis as defined in claim 1, wherein the textile substrate is a woven single-velour tubular structure.

14. A soft-tissue prosthesis as defined in claim 1, wherein the textile substrate is a woven singular-velour tubular structure having a velour on an outer surface of said textile substrate.

* * * * *